United States Patent
Zhuang et al.

(10) Patent No.: US 11,778,906 B2
(45) Date of Patent: Oct. 3, 2023

(54) ELECTRON TRANSPORT MATERIAL AND APPLICATION THEREOF

(71) Applicant: GUANGDONG JUHUA PRINTED DISPLAY TECHNOLOGY CO., LTD., Guangzhou (CN)

(72) Inventors: Jinyong Zhuang, Guangzhou (CN); Ying Chen, Guangzhou (CN)

(73) Assignee: GUANGDONG JUHUA PRINTED DISPLAY TECHNOLOGY CO. LTD, Guangzhou (CN)

( * ) Notice: Subject to any disclaimer, the term of this patent is extended or adjusted under 35 U.S.C. 154(b) by 412 days.

(21) Appl. No.: 17/265,074

(22) PCT Filed: Dec. 29, 2018

(86) PCT No.: PCT/CN2018/125620
§ 371 (c)(1),
(2) Date: Feb. 1, 2021

(87) PCT Pub. No.: WO2020/024557
PCT Pub. Date: Feb. 6, 2020

(65) Prior Publication Data
US 2021/0328151 A1    Oct. 21, 2021

(30) Foreign Application Priority Data
Aug. 3, 2018 (CN) .......................... 201810878226.X

(51) Int. Cl.
*C07D 251/24* (2006.01)
*C07D 403/10* (2006.01)
(Continued)

(52) U.S. Cl.
CPC ......... *H10K 85/654* (2023.02); *H10K 85/626* (2023.02); *H10K 85/6572* (2023.02); *H10K 50/16* (2023.02)

(58) Field of Classification Search
CPC .................................................. C07D 251/24
See application file for complete search history.

(56) References Cited

U.S. PATENT DOCUMENTS

2017/0244044 A1    8/2017   Ikeda et al.

FOREIGN PATENT DOCUMENTS

| CN | 1867646 A | 11/2006 | |
| CN | 107001925 A * | 8/2017 | ........... C07D 498/12 |

(Continued)

OTHER PUBLICATIONS

Computer-generated English-language translation of JP-2004022334-A.*

(Continued)

*Primary Examiner* — Vu A Nguyen
(74) *Attorney, Agent, or Firm* — Dorsey & Whitney LLP

(57) ABSTRACT

The present disclosure relates to an electron transport material and an application thereof. According to the electron transport material, a structure of a molecular is designed and selected to be constructed by a group having a high carrier mobility, such that the molecule has a higher carrier mobility. In addition, a core group of the molecule is a structure based on mesitylene triazine. The molecular rigidity of the structure is strong, and the intermolecular stacking can be effectively inhibited, such that the material has a lower refractive index, and the surface plasma polariton loss of an organic light-emitting device can be effectively suppressed. The forward light-emitting efficiency of the light-emitting device can be improved by more than 14% by applying the electron transport material to the device.

17 Claims, 1 Drawing Sheet

(51) Int. Cl.
*C07D 405/10* (2006.01)
*C07D 409/10* (2006.01)
*C07D 493/04* (2006.01)
*C07D 495/04* (2006.01)
*H01L 51/00* (2006.01)
*H01L 51/50* (2006.01)
*H10K 85/60* (2023.01)
*H10K 50/16* (2023.01)

(56) References Cited

FOREIGN PATENT DOCUMENTS

| CN | 107001925 A | | 8/2017 | |
|---|---|---|---|---|
| JP | 2003045662 A | | 2/2003 | |
| JP | 200422334 A | | 1/2004 | |
| JP | 2004022334 A | * | 1/2004 | ............. H05B 33/14 |
| JP | 2004253298 A | | 9/2004 | |
| JP | 20070137829 A | | 6/2007 | |
| JP | 2007314503 A | | 12/2007 | |
| JP | 2017518281 A | | 7/2017 | |
| JP | 2017155003 A | | 9/2017 | |
| KR | 20160049844 A | * | 5/2016 | ............. C09K 11/06 |
| KR | 20160049844 A | | 5/2016 | |
| WO | WO-2015175678 A1 | * | 11/2015 | ........... C07C 225/22 |

OTHER PUBLICATIONS

International Search Report from International Application No. PCT/CN2018/125620 dated Apr. 9, 2019.

* cited by examiner

ELECTRON TRANSPORT MATERIAL AND APPLICATION THEREOF

CROSS-REFERENCE TO RELATED APPLICATION

This application is a U.S. National Stage of PCT International Application No. PCT/CN2018/125620 filed on Dec. 29, 2018, which claims the priority to a Chinese patent application No. 201810878226.X, entitled "Electron transport material and application thereof", and filed on Aug. 3, 2018 with Chinese Patent office, the disclosure of each of which is herein incorporated in its entirety by reference.

TECHNICAL FIELD

This disclosure relates to the field of organic conductive materials, in particular to an electron transport material and its application.

BACKGROUND

In OLED devices, under the action of current, the organic molecules having light-emitting function realize the compound of a hole and an electron, and emit light in random direction in the form of dipole. However, not all the emitted light can be used for lighting or display. Only a part of the light can reach the outside of the substrate, and a large part of the light is lost in the device in various forms. The main forms of the loss are: a SPP (surface plasma polariton) loss caused by the metal electrodes, a Wave Guide loss caused by a high refractive index of an organic layer and ITO etc., and a substrate loss caused by total reflection at the interface between a substrate material and the air. These losses add up, such that the light output efficiency of OLED with ordinary planar structure is far less than 100%. According to the optical calculation, the luminous efficiency of the emitting OLED device with traditional planar bottom is only about 22%. This means that even if other performances of the device, such as internal quantum efficiency and electrical balance of the material, are optimal, the external quantum efficiency (EQE) still will not be very high, and most of the light emitted is lost in the device.

According to the theoretical calculation, the surface plasma state loss often accounts for about 30% of the total emitted light in a conventional planar OLED device, which even exceeds the luminous efficiency that an OLED device generally could reach. Therefore, some schemes to reduce the surface plasma state loss have been proposed. For example, a microstructure is added in a device (such as metal electrodes and organic layers) to reduce the surface plasma loss and wave guide loss, which is proved as an effective method by experiments. Such method can increase the external quantum efficiency by about 10%-30%. However, due to the complex manufacture process of the microstructure, there are still many challenges for applying to the actual industry, such as low yield and high cost caused by the complexity of the technology.

SUMMARY OF THE INVENTION

Based on this, it is necessary to provide an electron transport material and its application which can effectively suppress the surface plasma state loss of organic light-emitting device and improve the forward luminous efficiency of the device.

An electron transport material includes a compound represented by the general formula I,

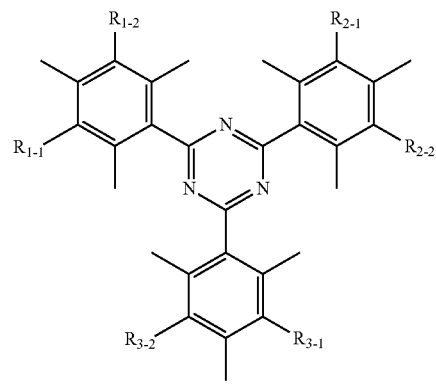

I wherein, $R_{1-1}$, $R_{1-2}$, $R_{2-1}$, $R_{2-2}$, $R_{3-1}$ and $R_{3-2}$ are each independently selected from hydrogen and one of the following groups represented by formulas 1-1 to 1-16, $R_{1-1}$ and $R_{1-2}$ are not simultaneously hydrogen, $R_{2-1}$ and $R_{2-2}$ are not simultaneously hydrogen, and $R_{3-1}$ and $R_{3-2}$ are not simultaneously hydrogen,

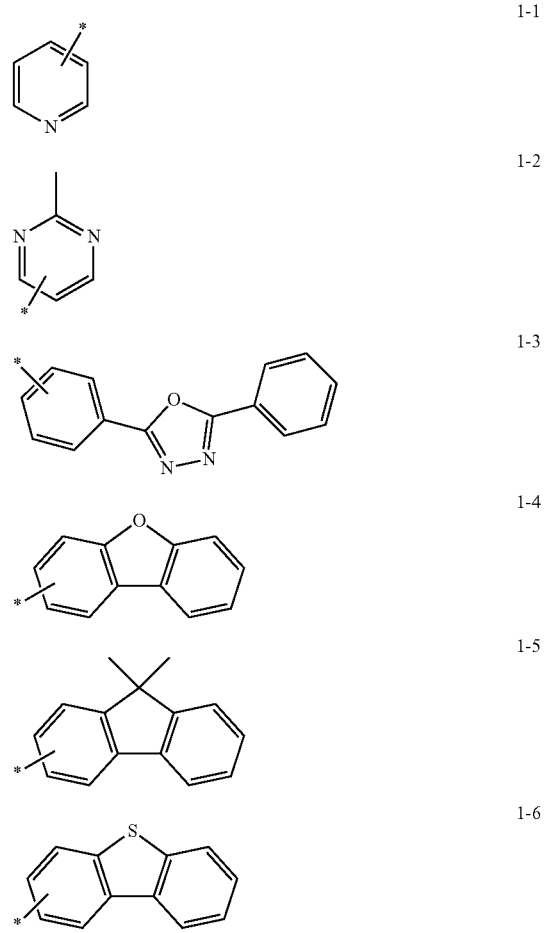

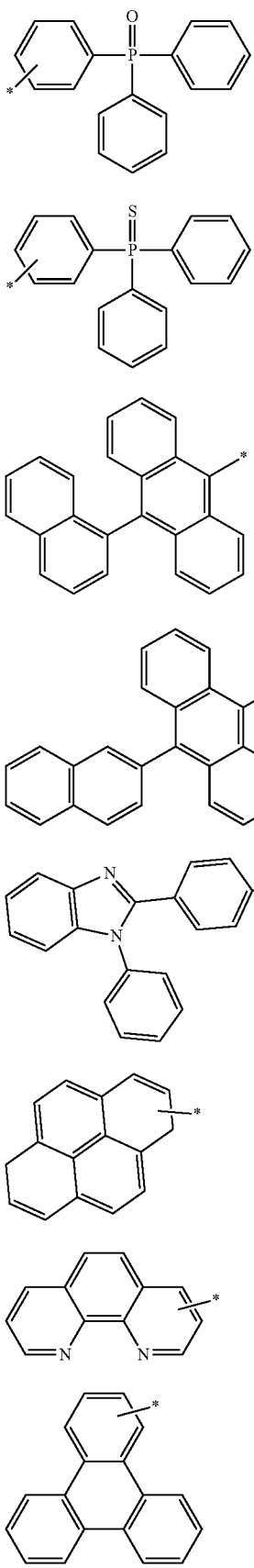

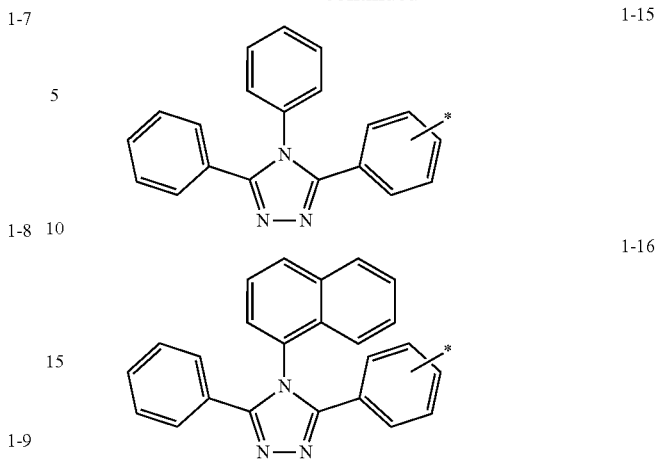

wherein, * denotes the binding sites of $R_{1-1}$, $R_{1-2}$, $R_{2-1}$, $R_{2-2}$, $R_{3-1}$ and $R_{3-2}$ with the benzene ring on the compound represented by the general formula I.

This disclosure further provides an application of the electron transport material in the manufacture of semiconductor devices.

This disclosure further provides a semiconductor device containing the electron transport material.

This disclosure further provides a display device having a light-emitting device, and the light-emitting device contains the electron transport material.

Compared with the existing scheme, this disclosure has the following beneficial effects:

For the above-mentioned electron transport material, the structure of a molecular is designed and selected to be constructed by a group having a high carrier mobility, such that the molecule has a higher carrier mobility. In addition, a core group of the molecule is a structure based on mesitylene triazine. The molecular rigidity of the structure is strong, and the intermolecular stacking can be effectively inhibited, such that the material has a lower refractive index and the surface plasma state loss of an organic light-emitting device can be effectively suppressed. Compared with the commonly used electron transport material TPBi, when applied in a light-emitting device, this electron transport material can improve the forward luminous efficiency by more than 14%.

DETAILED DESCRIPTION

Figure 1:
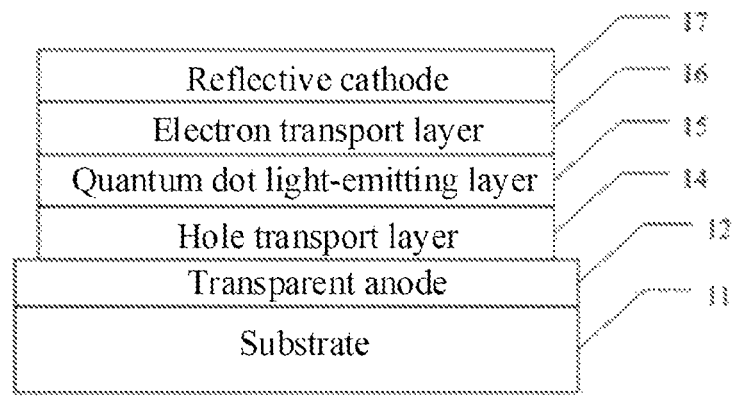
FIG. 1 is a structure diagram of a quantum dot light-emitting diode according to some embodiments.

In order to facilitate the understanding of the disclosure, a more comprehensive description of the disclosure will be given in combination with the embodiment below. However, the present disclosure may be implemented in many different forms and is not limited to the embodiments described herein. On the contrary, these embodiments are provided for a more thorough and comprehensive understanding of the content of the disclosure.

Unless otherwise defined, all technical and scientific terms used herein have the same meanings as those commonly understood by those skilled in the technical field of the present disclosure. The terms used in the specification of the present disclosure are only for the purpose of describing specific embodiments, and are not intended to limit the disclosure.

The electron transport material of an embodiment of the disclosure comprises a compound represented by the general formula I, general formula I:

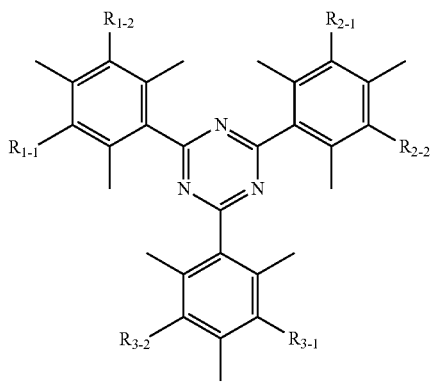

wherein, $R_{1-1}$, $R_{1-2}$, $R_{2-1}$, $R_{2-2}$, $R_{3-1}$ and $R_{3-2}$ are each independently selected from hydrogen and one of the groups represented by formulas 1-1 to 1-16, $R_{1-1}$ and $R_{1-2}$ are not simultaneously hydrogen, $R_{2-1}$ and $R_{2-2}$ are not simultaneously hydrogen, and $R_{3-1}$ and $R_{3-2}$ are not simultaneously hydrogen, 1-1

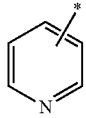

1-2

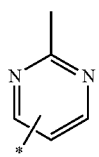

1-3

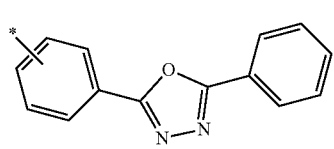

1-4

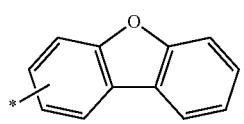

1-5

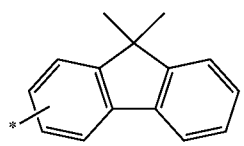

1-6

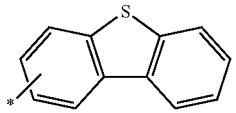

1-7

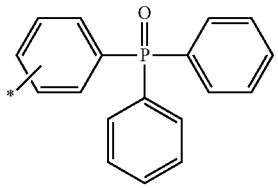

1-8

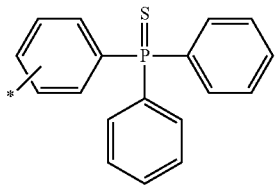

1-9

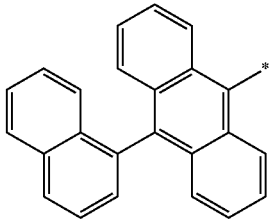

1-10

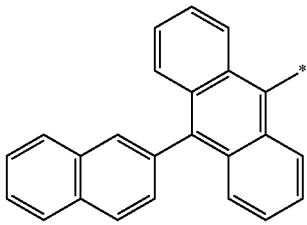

1-11

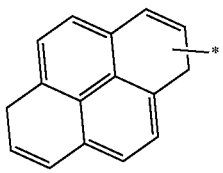

1-12

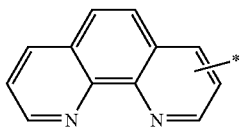

1-13

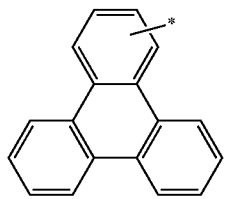

1-14

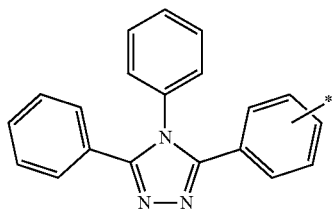

1-15

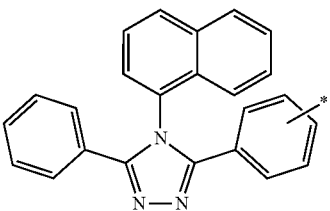

1-16 wherein, * denotes the binding sites of $R_{1-1}$, $R_{1-2}$, $R_{2-1}$, $R_{2-2}$, $R_{3-1}$ and $R_{3-2}$ with a benzene ring on the compound represented by the general formula I. Each of the above-mentioned groups is a group with a higher electron transport ability.

In one example, $R_{1-1}$, $R_{1-2}$, $R_{2-1}$, $R_{2-2}$, $R_{3-1}$ and $R_{3-2}$ are each independently selected from hydrogen and one of the groups represented by formulas 1-9 to 1-11. Each of the groups represented by formulas 1-9 to 1-11 has a lower refractive index and a more outstanding electron transport ability.

In one example, $R_{1-1}$ or $R_{1-2}$ is hydrogen, $R_{2-1}$ or $R_{2-2}$ is hydrogen, and $R_{3-1}$ or $R_{3-2}$ is hydrogen.

In one example, the compound represented by the general formula I is selected from one of compound 1 to compound 10:

Compound 1

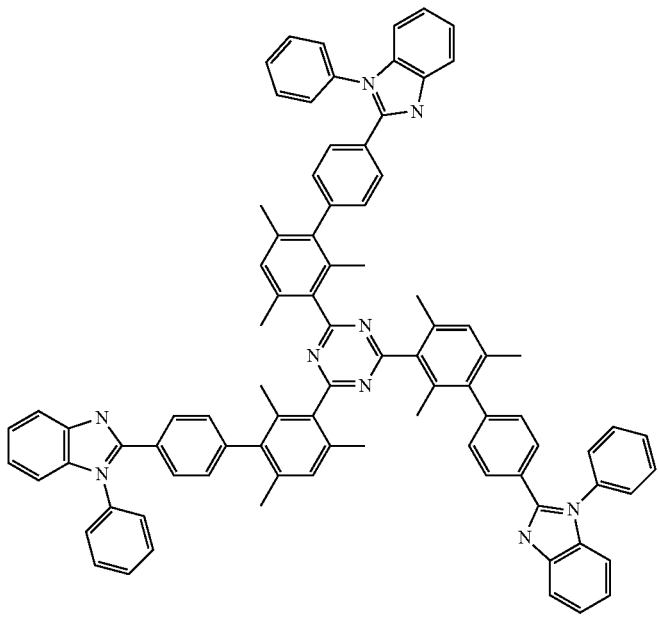

-continued
Compound 2
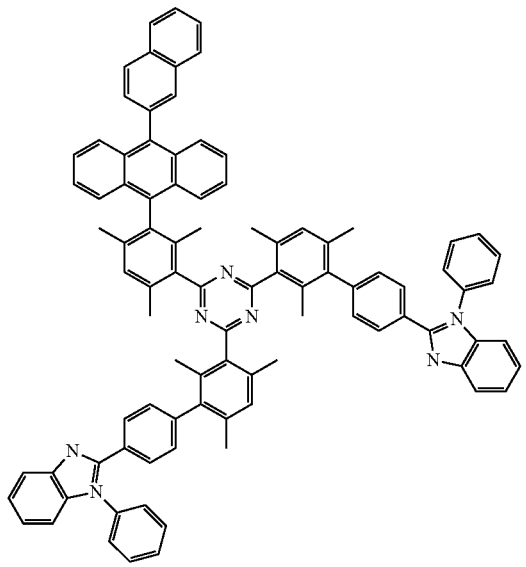
Compound 3
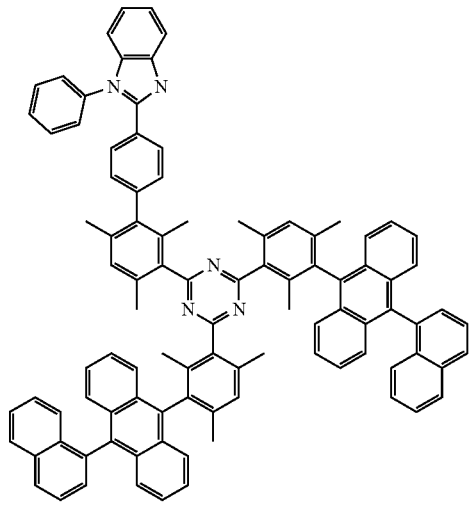
Compound 4
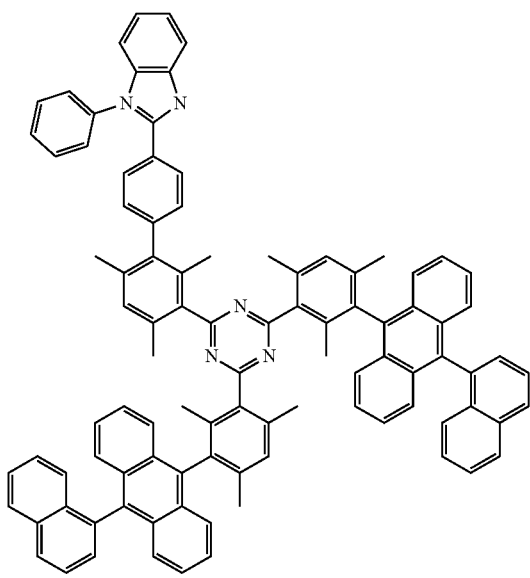
Compound 5
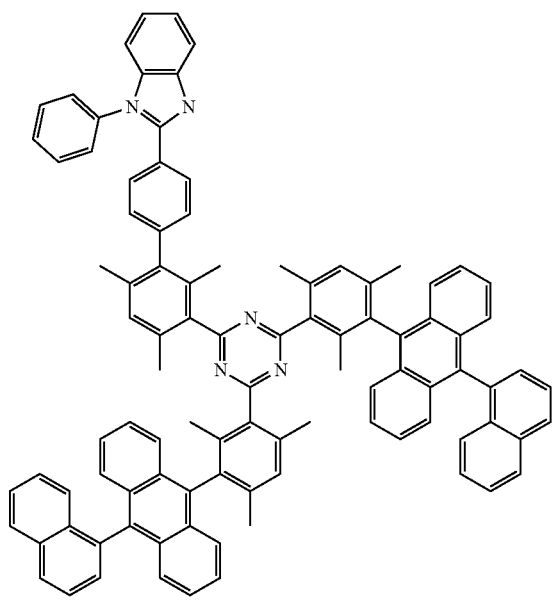

Compound 6
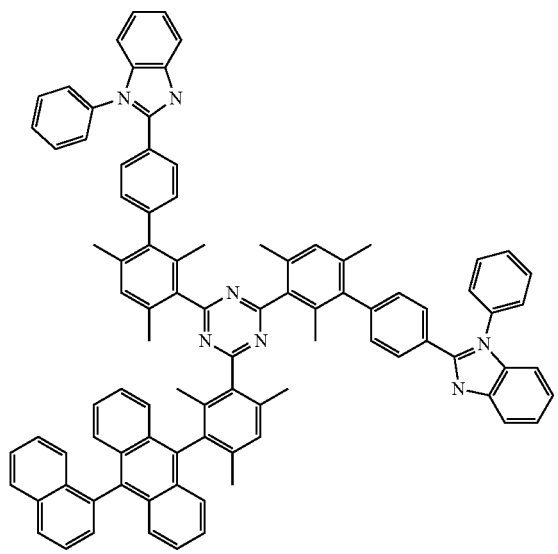
Compound 7
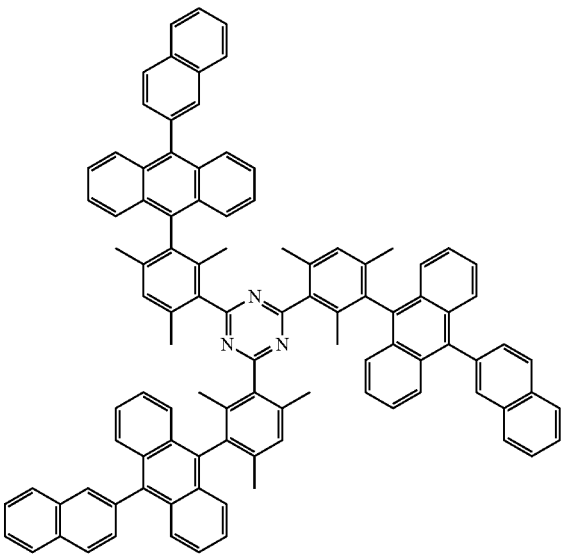
Compound 8
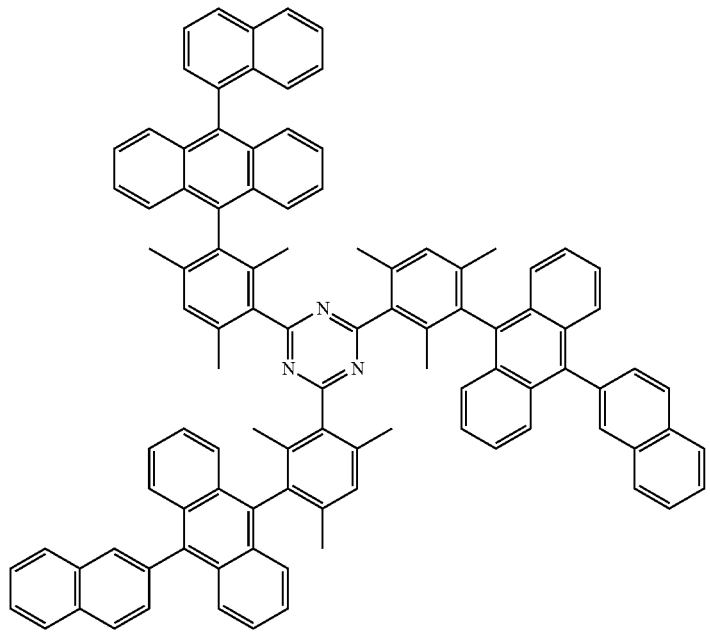

-continued

Compound 9

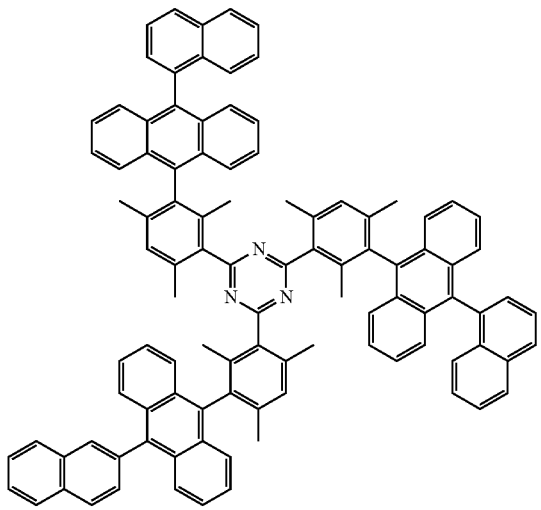

Compound 10

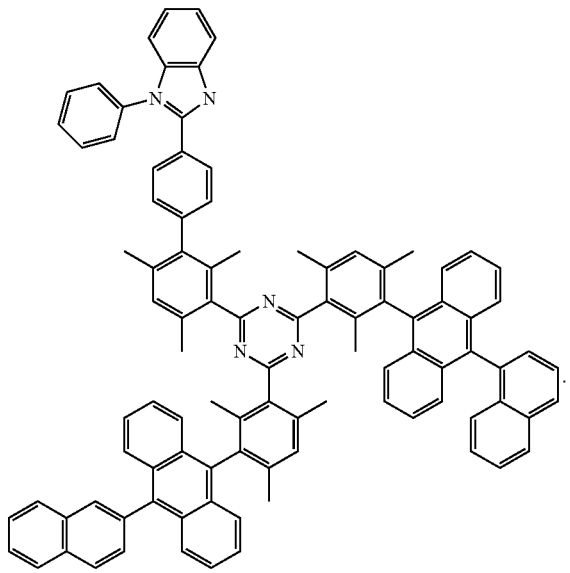

Each of the above-mentioned compound 1 to compound 10 has a more outstanding carrier mobility and a lower refractive index.

Further, the compound represented by general formula I is selected from compound 1, compound 4 or compound 7.

Further, the present embodiment also provides an application of any of the above-mentioned electron transport materials in the manufacture of semiconductor devices.

Further, the present embodiment also provides a semiconductor device containing an electron transport material of any of the above examples.

Optionally, the semiconductor device may be, but is not limited to, an organic light-emitting diode (OLED), a quantum dot light-emitting diode (QLED), an organic photovoltaic cell (OPV), or an organic light-emitting field-effect transistor (OTFT).

Further, the present embodiment also provides a display device having a light-emitting device which contains an electron transport material of any of the above examples. The light-emitting device is an organic light-emitting diode and/or a quantum dot light-emitting diode. In some specific embodiments, the material of an electron transport layer of the organic light-emitting diode and/or quantum dot light-emitting diode includes a compound represented by the general formula I in any of the above examples.

As shown in FIG. 1, in some specific embodiments, the quantum dot light-emitting diode, from bottom to top in sequence, includes: a PET substrate 11, an ITO transparent anode 12, a poly-TPD hole transport layer 14, a quantum dot light-emitting layer 15, an electron transport layer 16, and a reflective Al reflective cathode 17. The electron transport layer 16 includes a compound represented by the general formula I in any of the above examples.

Figure 2:
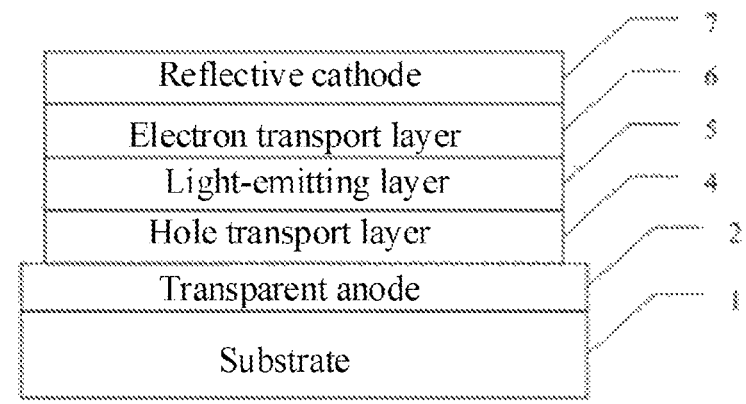
FIG. 2 is a structure diagram of an organic light-emitting diode according to some embodiments.

As shown in FIG. 2, in some specific embodiments, the organic light-emitting diode (OLED), from bottom to top in sequence, includes: a PET substrate 1, an ITO transparent anode 2, a NPD (N, N-dinaphthyl-N, N'-diphenylbenzidine) hole transport layer 4, an organic light-emitting layer 5, an electron transport layer 6, and a reflective Ag reflective cathode 7. The electron transport layer 6 includes a compound represented by the general formula I in any of the above examples.

In one example, the display device is a bottom emitting type display panel, such as a bottom emitting type OLED display panel or a bottom emitting type QLED panel.

The above-mentioned electron transport material has the characteristics of low refractive index and high mobility. Therefore, it can effectively improve the forward luminous efficiency of the device by applying the material in the light-emitting device, that is, the external quantum efficiency of the device can be improved. Specifically, the structure of a molecular of above-mentioned electron transport material is designed and selected to be constructed by a group having a high carrier mobility, such that the molecule has a higher carrier mobility. In addition, a core group of the molecule is a structure based on mesitylene triazine. The molecular rigidity of the structure is strong, and the intermolecular stacking can be effectively inhibited, such that the material has a lower refractive index and the surface plasma state loss of a light-emitting diodes, an organic light-emitting diode (OLED) and a quantum dot light-emitting diode (QLED) can be effectively suppressed.

The present disclosure will be described in combination with the embodiment of synthesis reaction. However, the disclosure is not limited to the following examples. It should be understood that the scope of the disclosure is summarized in the attached claims. Under the guidance of the concept of the disclosure, those skilled in the art shall realize that certain changes made to various embodiments of the disclosure will be covered by the spirit and scope of the claims of the disclosure.

Example 1

Synthesis of Compound 1

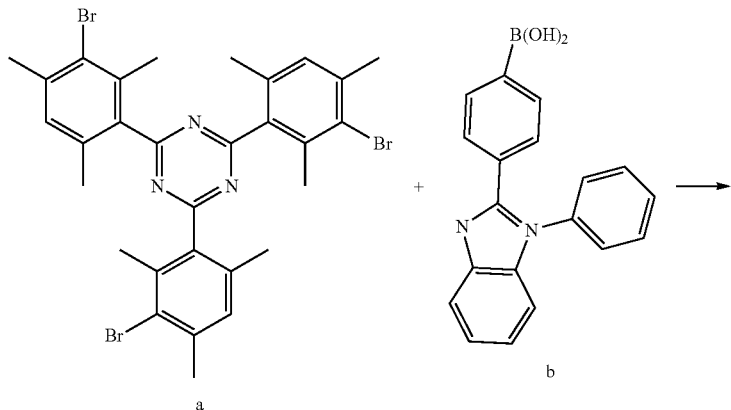

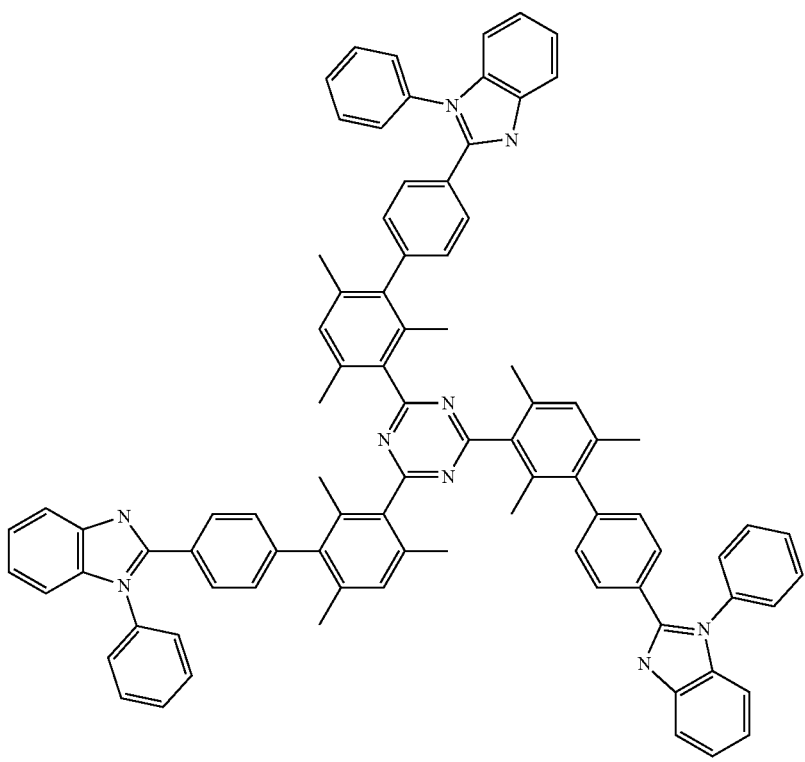

An 8.5 g (12.6 mmol) of intermediate a (bromo mesitylene triazine), a 13.96 g (44.3 mmol) of intermediate b (Phenylbenzimidazole boric acid), a 0.51 g (0.44 mmol) of tetrakis (triphenylphosphine) palladium catalyst, a 6.3 ml of 2M potassium carbonate solution, a 100 ml of toluene and a 25 ml of ethanol are weighted and added into a 500 ml three necked flask, respectively, which is heated under the protection of nitrogen until refluxing and is stirred overnight. After the reaction stopped and being cooled to the room temperature, the solvent is extracted with dichloromethane, and the organic phase is retained. Then the solvent is spin-dried after dried with anhydrous magnesium sulfate. The crude product is separated by silica gel column chromatography, and the eluent is dichloromethane/n-hexane. Then the pure product of compound 1 with 6.30 g is obtained, and the yield is 40%. C87H72N9, Exact Mass: 1242.59. Found: 1243.56; Elemental Analysis: C, 84.03; H, 5.84; N, 10.14.

Example 2

Synthesis of Compound 4

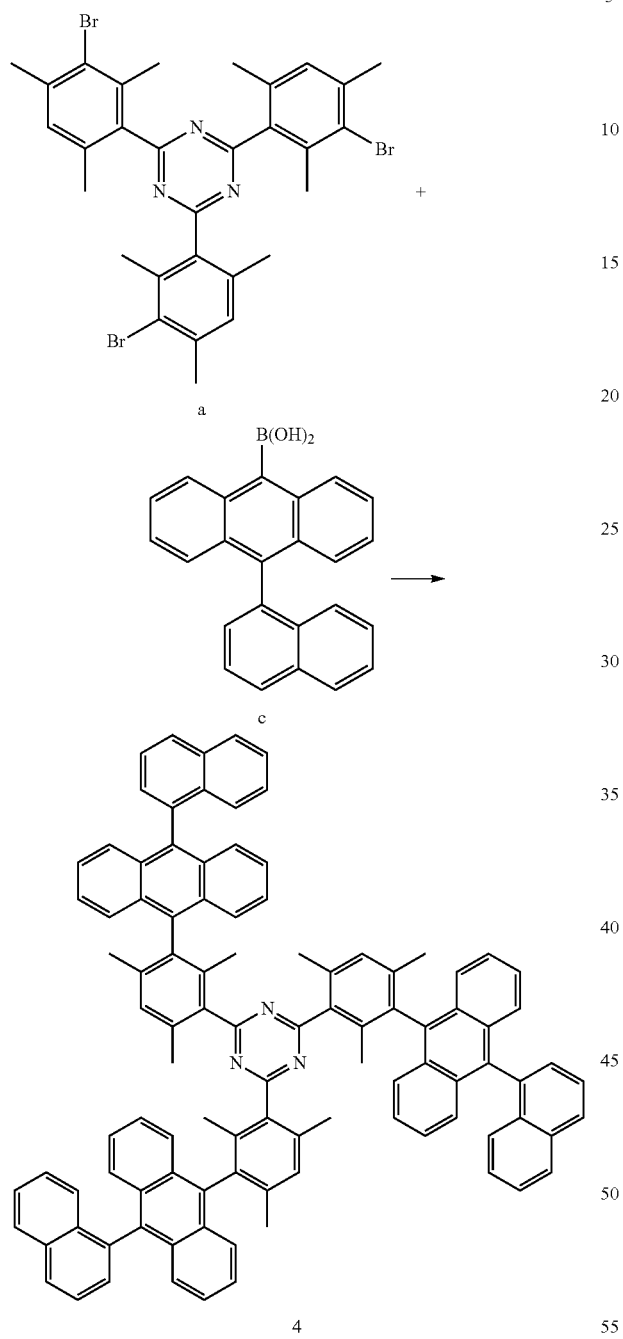

A 7.6 g (11.3 mmol) of intermediate a (bromo mesitylene triazine), a 13.83 g (39.6 mmol) of intermediate c (anthracene boric acid), a 0.48 g (0.41 mmol) of tetrakis (triphenylphosphine) palladium catalyst, a 6.0 ml of 2M potassium carbonate solution, a 100 ml of toluene and a 25 ml of ethanol are weighted and added into a 500 ml three necked flask, respectively, which is heated under the protection of nitrogen until refluxing and is stirred overnight. After the reaction stopped and being cooled to the room temperature, the solvent is extracted with dichloromethane, and the organic phase is retained. Then the solvent is spin-dried after dried with anhydrous magnesium sulfate. The crude product is separated by silica gel column chromatography, and the eluent is dichloromethane/n-hexane. Then the pure product of compound 4 with 6.83 g is obtained and the yield is 45%. $C_{102}H_{75}N_3$, Exact Mass: 1342.71. Found: 1343.83; Elemental Analysis: C, 91.30; H, 5.54; N, 3.16.

Example 3

Synthesis of Compound 7

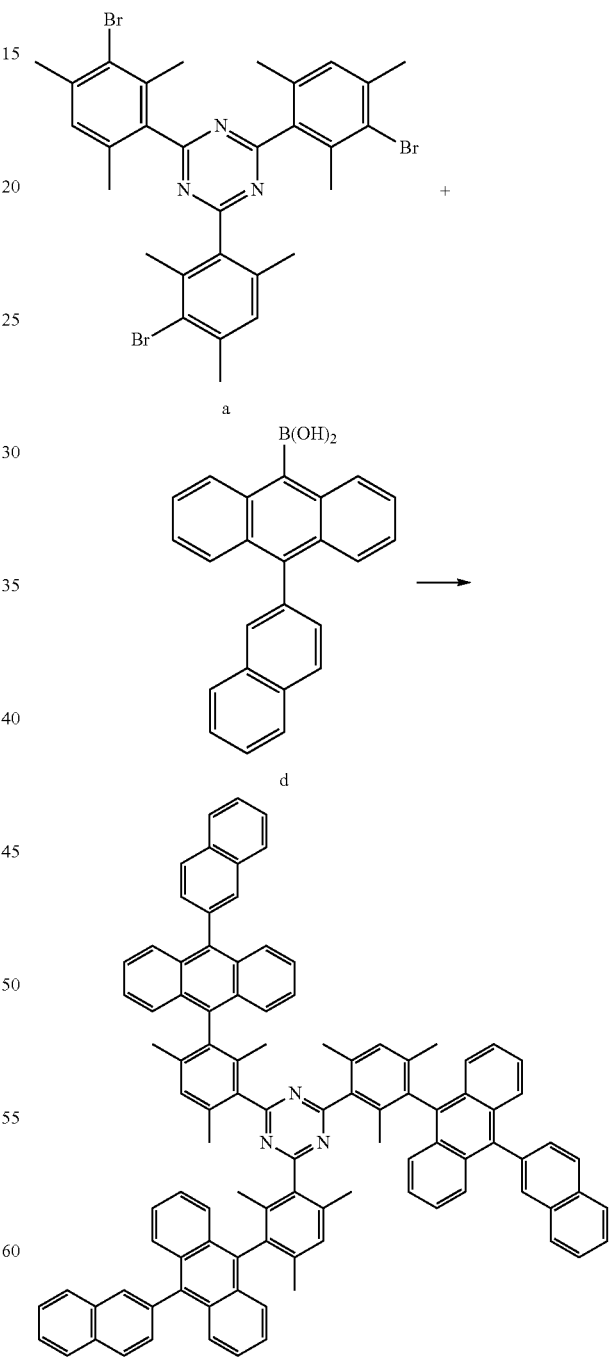

An 8.0 g (11.9 mmol) of intermediate a (bromo mesitylene triazine), a 14.5 g (41.6 mmol) of intermediate d (anthracene boric acid), a 0.49 g (0.42 mmol) of tetrakis (triphenylphosphine) palladium catalyst, a 6.1 ml of 2M potassium carbonate solution, a 100 ml of toluene and a 25 ml of ethanol are weighted and added into a 500 ml three neck flask, respectively, which is heated under the protection of nitrogen until refluxing and is stirred overnight. After the reaction stopped and being cooled to room temperature, the solvent is extracted with dichloromethane, and the organic phase is retained. Then the solvent is spin-dried after dried with anhydrous magnesium sulfate. The crude product is separated by silica gel column chromatography, and the eluent is dichloromethane/n-hexane. Then the pure product of compound 7 with 6.50 g is obtained and the yield is 41%. C102H75N3, Exact Mass: 1242.53. Found: 1243.59; Elemental Analysis: C, 84.02; H, 5.83; N, 10.15.

Example 4

Synthesis of Compound 8

An 8.0 g (11.9 mmol) of intermediate a (bromo mesitylene triazine), a 10.4 g (29.8 mmol) of intermediate d (anthracene boric acid), a 0.39 g (0.33 mmol) of tetrakis (triphenylphosphine) palladium catalyst, a 5.4 ml of 2M potassium carbonate solution, an 80 ml of toluene and an 18 ml of ethanol are weighted and added into a 500 ml three neck flask, respectively, which is heated under the protection of nitrogen until refluxing and is stirred overnight. After the reaction stopped and being cooled to the room temperature, the solvent is extracted with dichloromethane, and the organic phase is retained. Then the solvent is spin-dried after dried with anhydrous magnesium sulfate. The crude product is separated by silica gel column chromatography, and the eluent is dichloromethane/n-hexane. Then the pure product of intermediate f with 6.0 g is obtained, and the yield is 45%. C78H60BrN3, Exact Mass: 1119.24. Found: 1120.15; Elemental Analysis: C, 83.5; H, 5.6; Br, 7.14; N, 3.16.

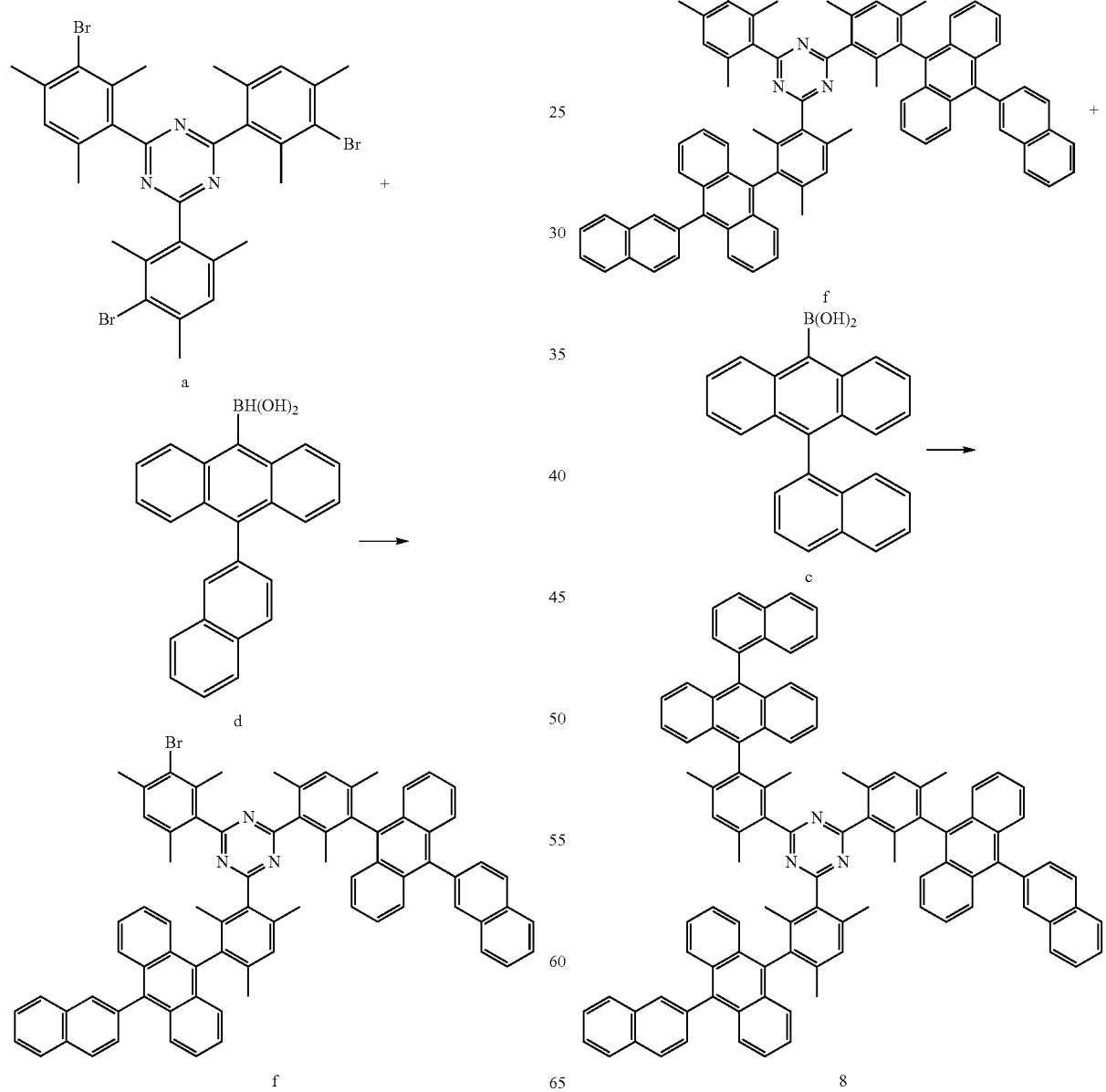

A 5.0 g (4.4 mmol) of intermediate f, a 4.8 g (8.9 mmol) of intermediate c (anthracene boric acid), a 0.30 g (0.26 mmol) of tetrakis (triphenylphosphine) palladium catalyst, a 4.3 ml of 2M potassium carbonate solution, a 50 ml of toluene and a 13 ml of ethanol are weighted and added into a 500 ml three necked flask, respectively, which is heated under the protection of nitrogen until refluxing and is stirred overnight. After the reaction stopped and being cooled to the room temperature, the solvent is extracted with dichloromethane, and the organic phase is retained. Then the solvent is spin-dried after dried with anhydrous magnesium sulfate. The crude product is separated by silica gel column chromatography, and the eluent is dichloromethane/n-hexane. Then the pure product of compound 8 with 4.4 g, and the yield is 81%. C102H75N3, Exact Mass: 1242.53. Found: 1243.59; Elemental Analysis: C, 84.02; H, 5.83; N, 10.15.

Other compounds involved in the disclosure can be synthesized by Suzuki coupling reaction, that is, halogenated mesitylene triazine reacts with boric acid compounds or borate ester compounds of groups of $R_{1-1}$, $R_{1-2}$, $R_{2-1}$, $R_{2-2}$, $R_{3-1}$ and $R_{3-2}$. Wherein, the atoms $X_{1-1}$ and $X_{1-2}$ on the halogenated mesitylene triazine can be H, F, Cl, Br or I atoms, while $X_{1-1}$ and $X_{1-2}$ cannot be H atoms simultaneously, as shown in the following formula:

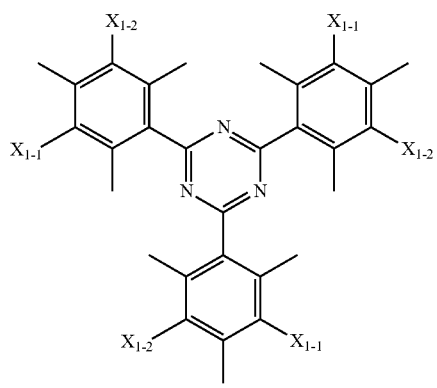

$X_{1-1}, X_{1-2}$: H, F, Cl, Br, I

Example 5

Compound 1 (ETM-1), compound 4 (ETM-4), compound 7 (ETM-7), compound 8 (ETM-8) and the commonly used electronic transport material TPBi are applied to the preparation and manufacture of OLEDs, the structures of each device are as follows:

ITO/NPB (40 nm)/CBP:Ir(ppy)3 (8 wt. %, 30 nm)/ETM-1/LiF (1 nm)/Al;
ITO/NPB (40 nm)/CBP:Ir(ppy)3 (8 wt. %, 30 nm)/ETM-4/LiF (1 nm)/Al;
ITO/NPB (40 nm)/CBP:Ir(ppy)3 (8 wt. %, 30 nm)/ETM-7/LiF (1 nm)/Al;
ITO/NPB (40 nm)/CBP:Ir(ppy)3 (8 wt. %, 30 nm)/ETM-8/LiF (1 nm)/Al;
ITO/NPB (40 nm)/CBP:Ir(ppy)3 (8 wt. %, 30 nm)/TPBi (30 nm)/LiF (1 nm)/Al.

Each functional layer in the device sample is prepared and manufactured by vacuum evaporation. The device sample performance data are summarized in the table below.

| Sample | Maximum current efficiency (cd/A) | Current efficiency at 1000 cd/m$^2$ brightness (cd/A) | Current density at 5V (mA/cm$^2$) | Brightness at 5V (cd/m$^2$) |
|---|---|---|---|---|
| ETM-1 | 44.8 | 27.5 | 4.3 | 1546 |
| ETM-4 | 42.3 | 26.3 | 4.3 | 1654 |
| ETM-7 | 43.5 | 27.8 | 4.4 | 1458 |
| ETM-8 | 43.0 | 27.3 | 4.4 | 1488 |
| TPBi  | 37.1 | 25.2 | 4.0 | 1009 |

It can be seen from the data in the table that compared with the commonly used electronic transport material TPBi, the maximum current efficiency can be increased by more than 14% by applying the electron transport material ETM-1, ETM-4, ETM-7 and ETM-8 of present disclosure in light-emitting devices. The electron transport material with a low refractive index and a high carrier mobility based on triazine group has obvious improving effect on OLEDs device efficiency.

Each technical feature of the above-mentioned embodiment can be arbitrarily combined. In order to make the description concise, all possible combinations of each technical feature in the above-mentioned embodiment are not described. However, as long as the combination of these technical features is not contradictory, it shall be considered as the scope of the description.

The above-mentioned embodiments only express several embodiments of the disclosure, and the description is more specific and detailed, but it can not be understood as a limitation on the scope of the disclosure. It should be pointed out that for ordinary technical personnel in the art, certain deformations and improvements can be made without departing from the concept of the disclosure, which belong to the protection scope of the disclosure. Therefore, the protection scope of the disclosure shall be subject to the attached claims.

What is claimed is:

1. An electron transport material, comprising:
a compound represented by a general formula I,

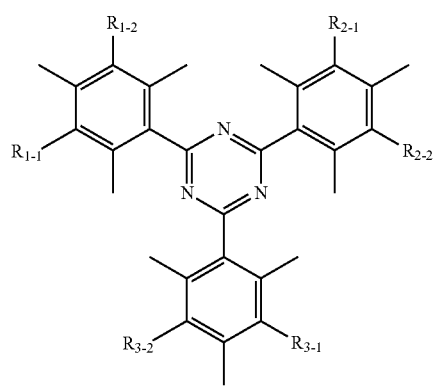

I wherein, $R_{1-1}$, $R_{1-2}$, $R_{2-1}$, $R_{2-2}$, $R_{3-1}$ and $R_{3-2}$ are each independently selected from hydrogen and one of the following groups represented by formulas 1-3 to 1-16, and $R_{1-1}$ and $R_{1-2}$ are not simultaneously hydrogen, $R_{2-1}$ and $R_{2-2}$ are not simultaneously hydrogen, and $R_{3-1}$ and $R_{3-2}$ are not simultaneously hydrogen,

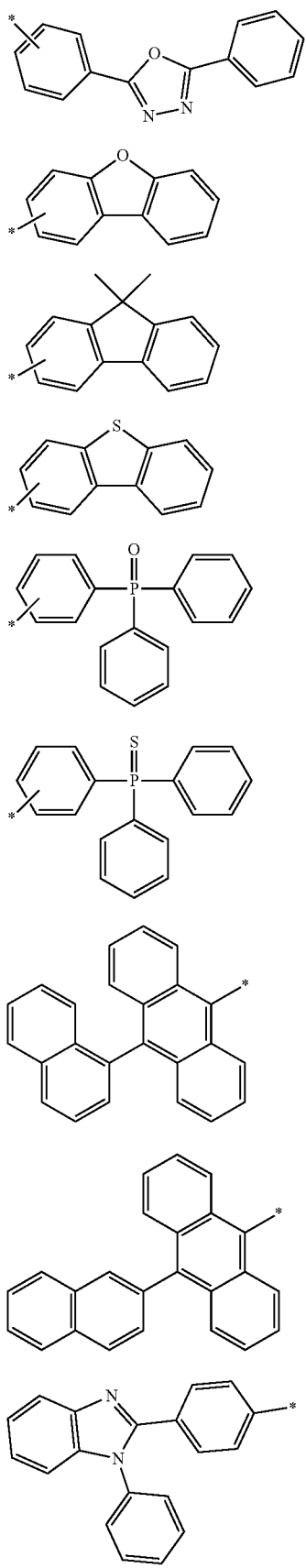

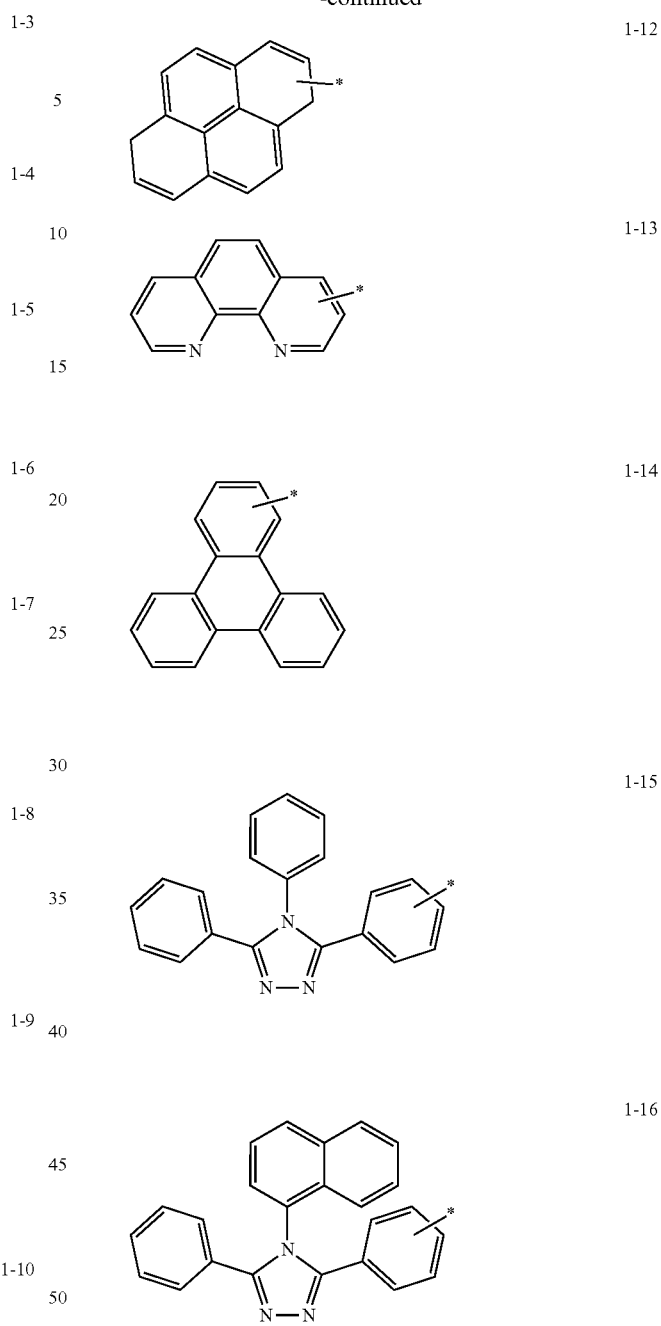

wherein, * denotes the binding sites of the $R_{1-1}$, $R_{1-2}$, $R_{2-1}$, $R_{2-2}$, $R_{3-1}$ and $R_{3-2}$ with a benzene ring on the compound represented by the general formula I.

2. The electron transport material according to claim 1, wherein $R_{1-1}$, $R_{1-2}$, $R_{2-1}$, $R_{2-2}$, $R_{3-1}$ and $R_{3-2}$ are each independently selected from hydrogen and one of the groups represented by formulas 1-9 to 1-11.

3. The electron transport material according to claim 1, wherein $R_{1-1}$ or $R_{1-2}$ is hydrogen, $R_{2-1}$ or $R_{2-2}$ is hydrogen, and $R_{3-1}$ or $R_{3-2}$ is hydrogen.

4. The electron transport material according to claim 1, wherein the compound represented by the general formula I is selected from one of compounds 1 to 10:

Compound 1
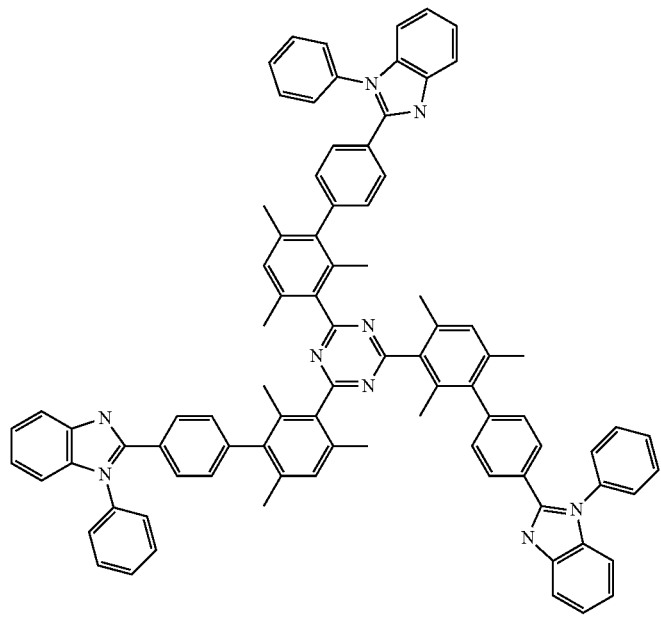
Compound 2
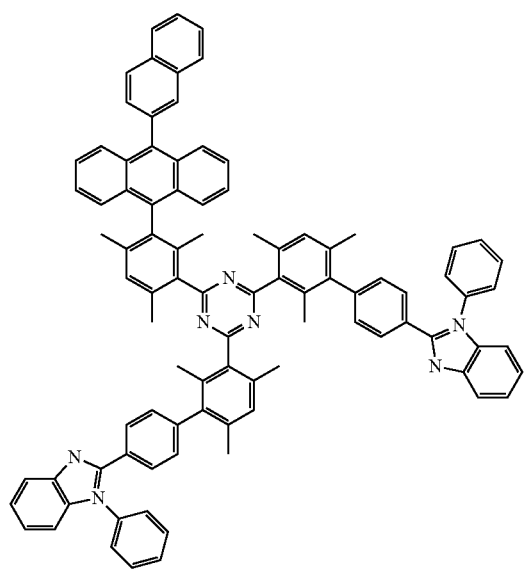
Compound 3
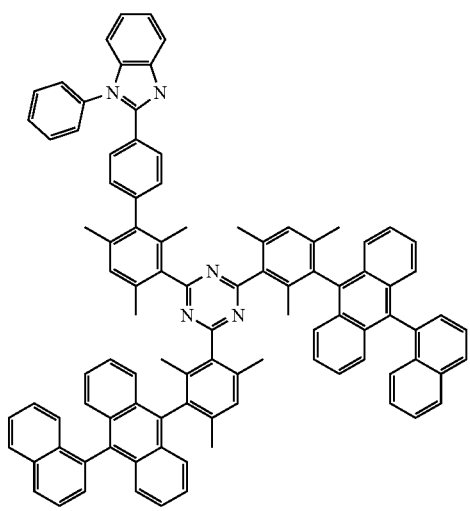

-continued
Compound 4
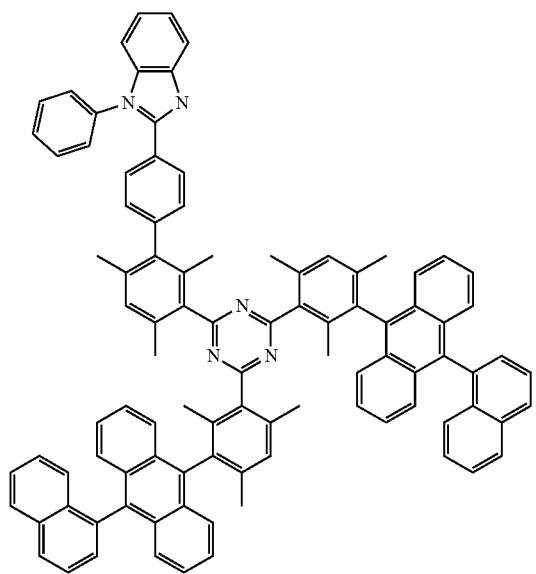
Compound 5
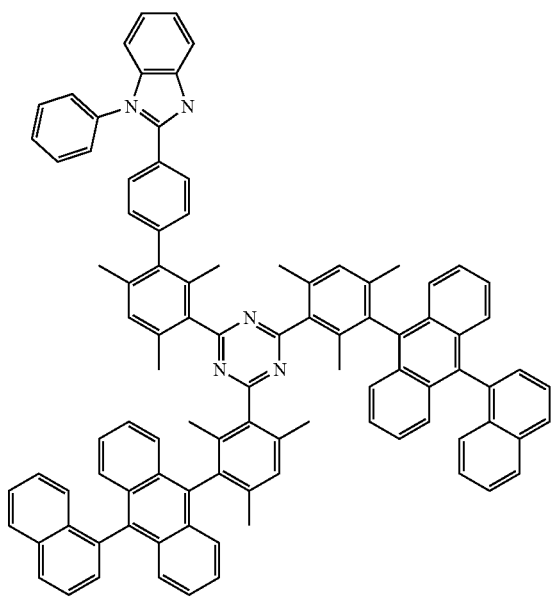
Compound 6
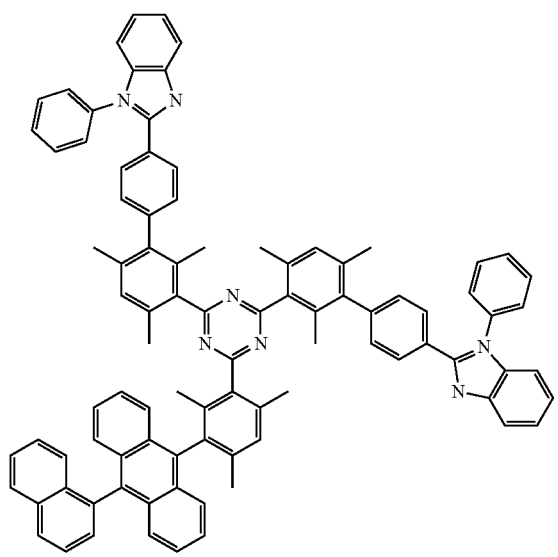
Compound 7
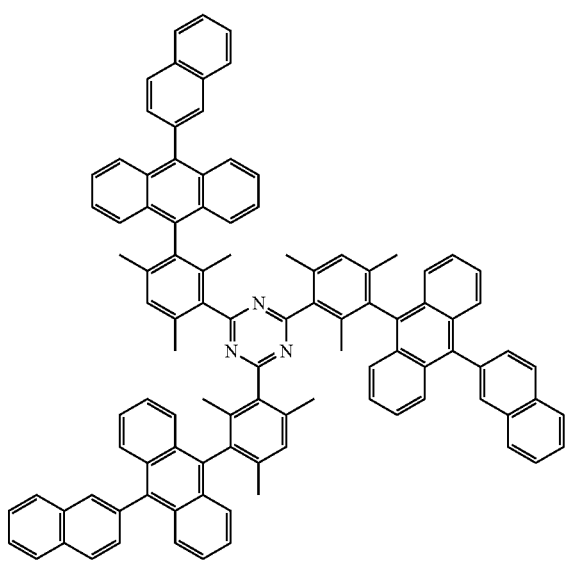

-continued
Compound 8
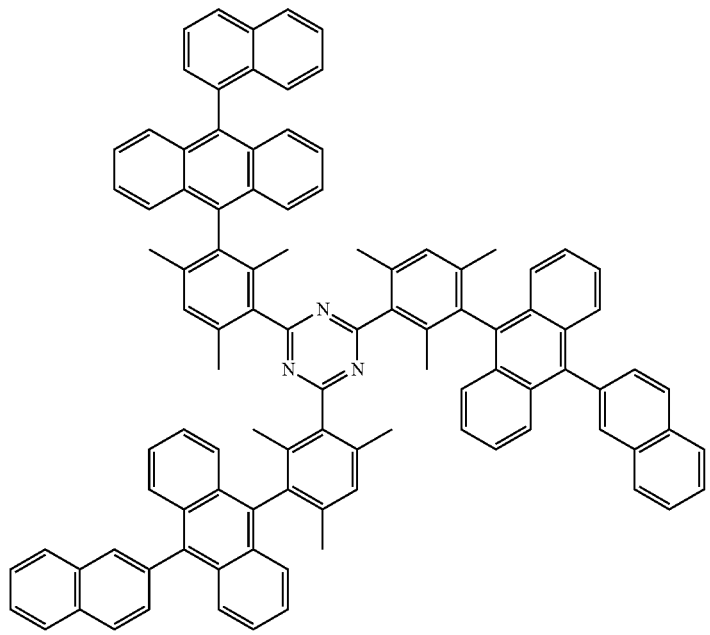
Compound 9
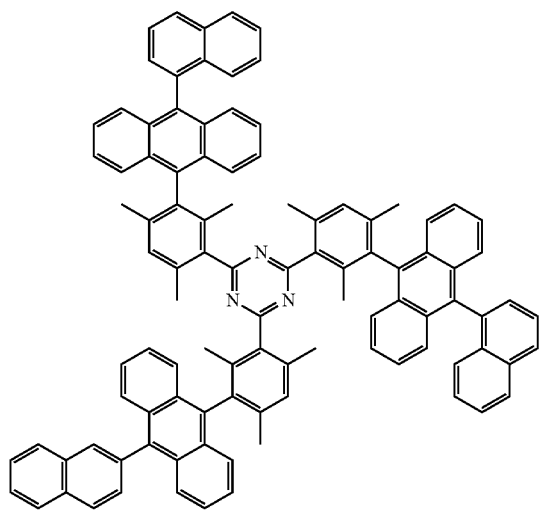
Compound 10
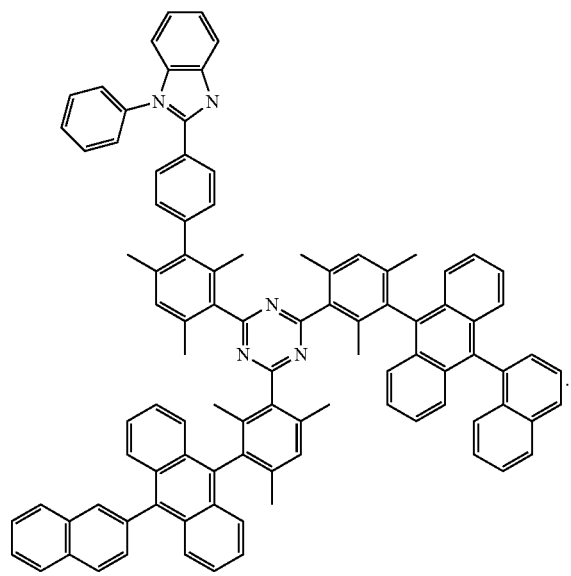

5. The electron transport material according to claim 4, wherein the compound represented by the general formula I is selected from compound 1, compound 4 or compound 7.

6. A semiconductor device, comprising an electron transport material, and the electron transport material comprises a compound represented by a general formula I,

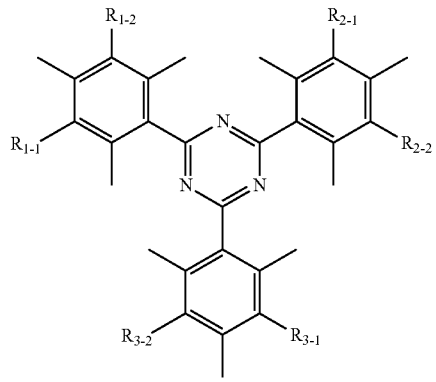

I wherein, $R_{1-1}$, $R_{1-2}$, $R_{2-1}$, $R_{2-2}$, $R_{3-1}$ and $R_{3-2}$ are each independently selected from hydrogen and one of the following groups represented by formulas 1-3 to 1-16, and $R_{1-1}$ and $R_{1-2}$ are not simultaneously hydrogen, $R_{2-1}$ and $R_{2-2}$ are not simultaneously hydrogen, and $R_{3-1}$ and $R_{3-2}$ are not simultaneously hydrogen, 1-3

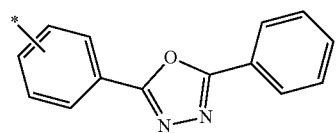

1-4

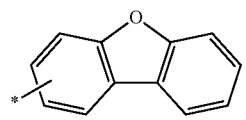

1-5

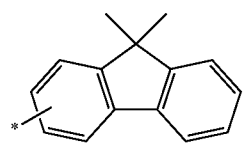

1-6

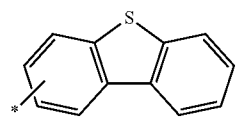

1-7

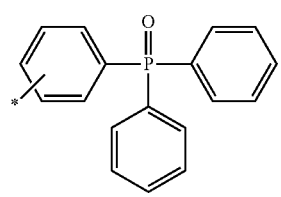

1-8

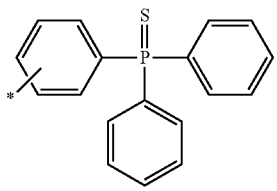

1-9

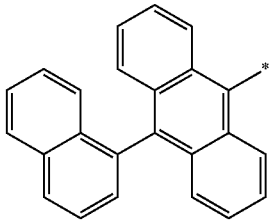

1-10

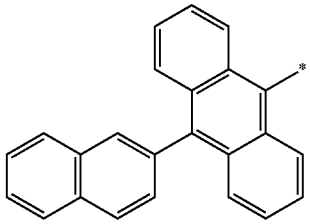

1-11

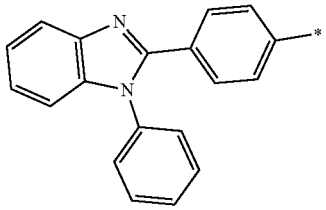

1-12

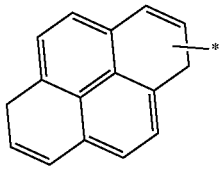

1-13

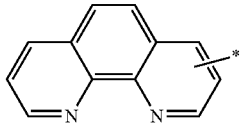

1-14

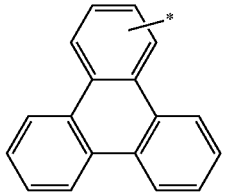

1-15

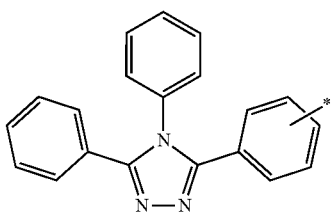

-continued 1-16

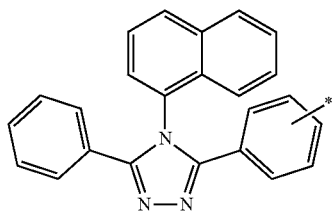

wherein, * denotes the binding sites of the $R_{1-1}$, $R_{1-2}$, $R_{2-1}$, $R_{2-2}$, $R_{3-1}$ and $R_{3-2}$ with a benzene ring on the compound represented by the general formula I.

7. The semiconductor device according to claim 6, wherein $R_{1-1}$, $R_{1-2}$, $R_{2-1}$, $R_{2-2}$, $R_{3-1}$ and $R_{3-2}$ are each independently selected from hydrogen and one of the groups represented by formulas 1-9 to 1-11.

8. The semiconductor device according to claim 6, wherein $R_{1-1}$ or $R_{1-2}$ is hydrogen, $R_{2-1}$ or $R_{2-2}$ is hydrogen, and $R_{3-1}$ or $R_{3-2}$ is hydrogen.

9. The semiconductor device according to claim 6, wherein the compound represented by the general formula I is selected from one of compounds 1 to 10:

Compound 1

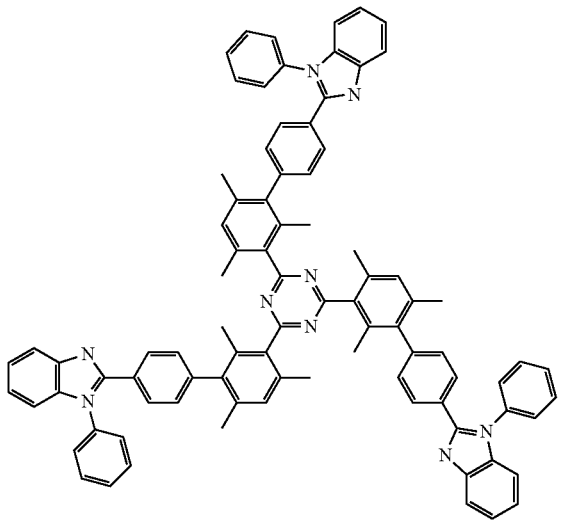

Compound 2

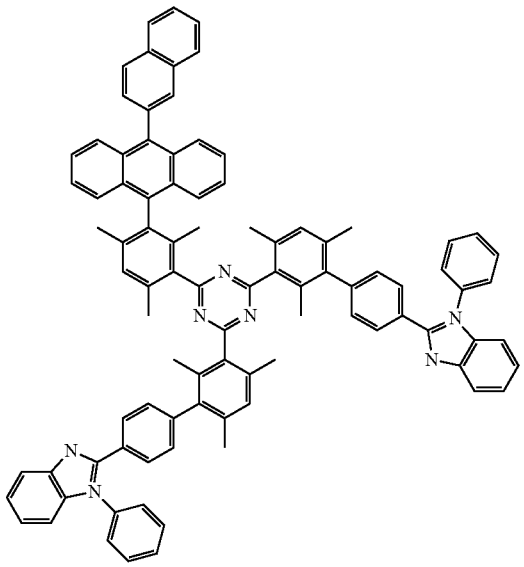

Compound 3

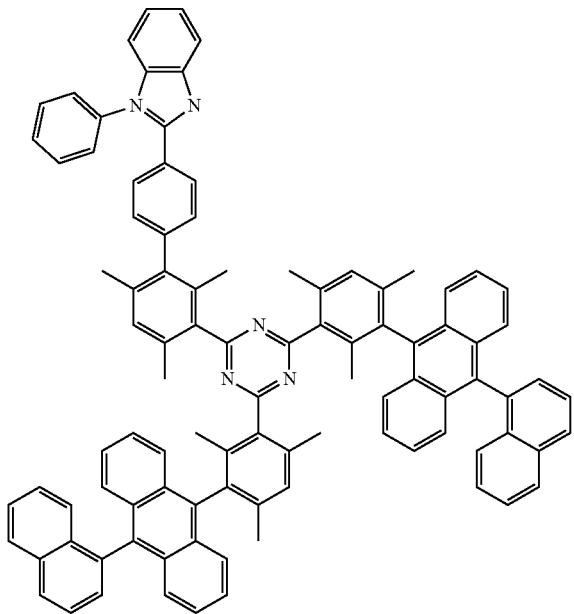

Compound 4
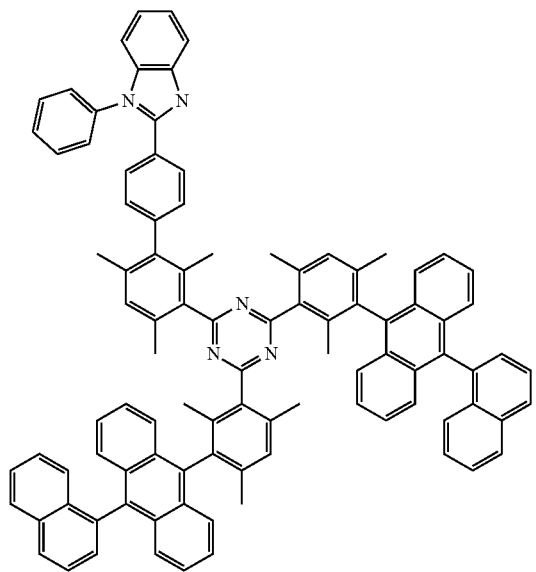
Compound 5
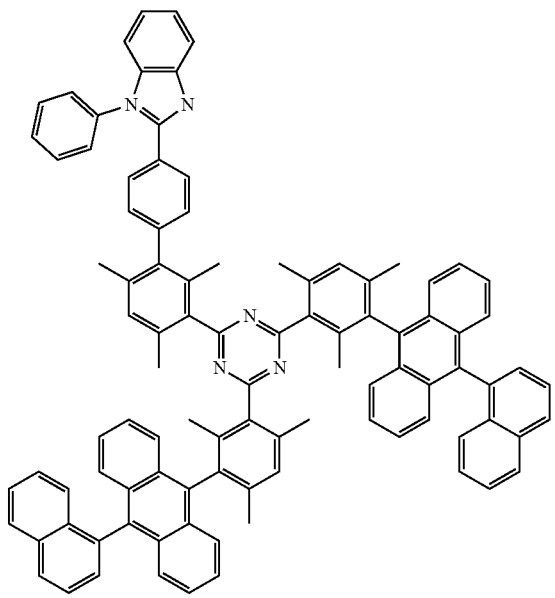
Compound 6
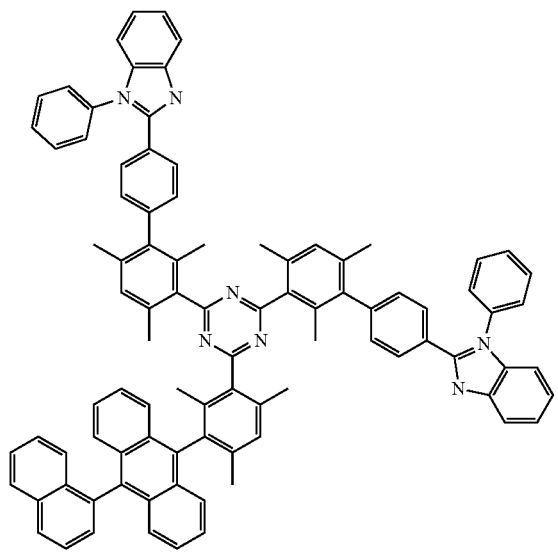
Compound 7
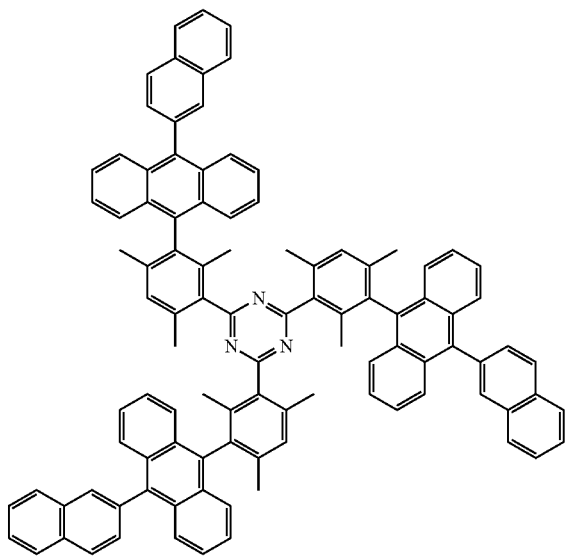

Compound 8
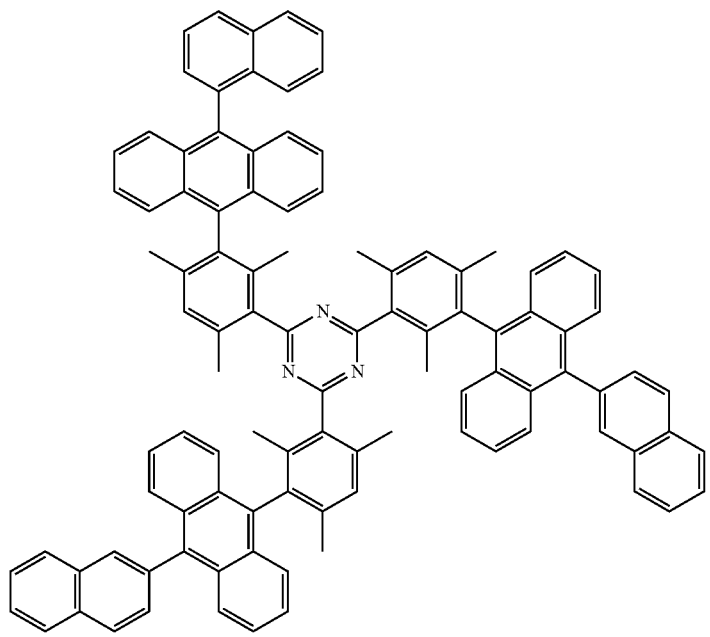
Compound 9
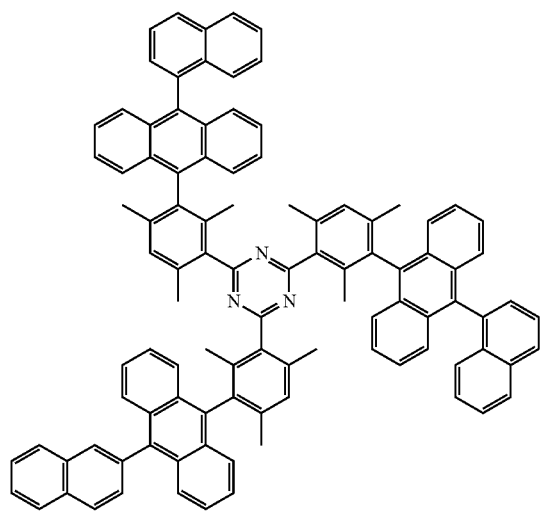
Compound 10
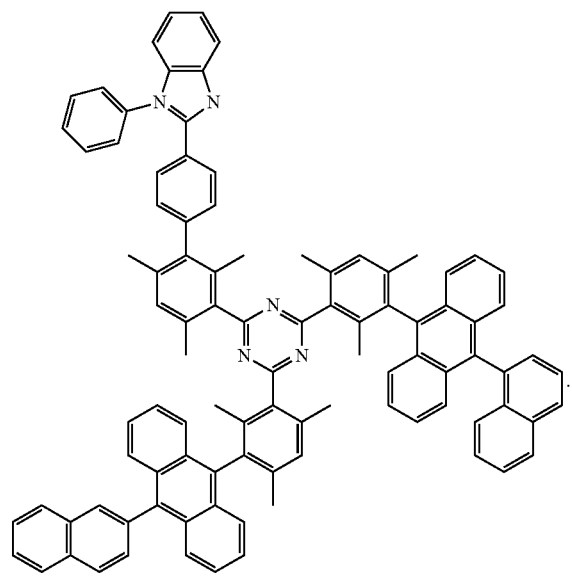

10. The semiconductor device according to claim 9, wherein the compound represented by the general formula I is selected from compound 1, compound 4 or compound 7.

11. The semiconductor device according to claim 6, wherein the semiconductor device is an organic light-emitting diode, a quantum dot light-emitting diode, an organic photovoltaic cell or an organic light-emitting field-effect transistor.

12. A display device having an organic light-emitting diode and/or a quantum dot light-emitting diode, wherein an electronic transport layer material of the organic light-emitting diode and/or the quantum dot light-emitting diode comprises a compound represented by a general formula I,

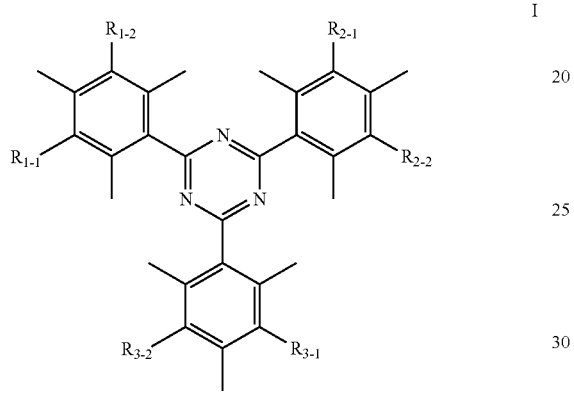

I wherein, $R_{1-1}$, $R_{1-2}$, $R_{2-1}$, $R_{2-2}$, $R_{3-1}$ and $R_{3-2}$ are each independently selected from hydrogen and one of the following groups represented by formulas 1-3 to 1-16, and $R_{1-1}$ and $R_{1-2}$ are not simultaneously hydrogen, $R_{2-1}$ and $R_{2-2}$ are not simultaneously hydrogen, and $R_{3-1}$ and $R_{3-2}$ are not simultaneously hydrogen,

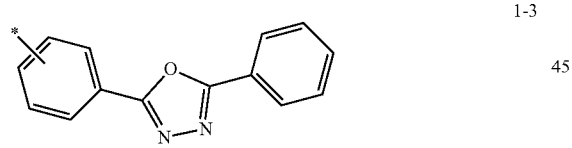

1-3

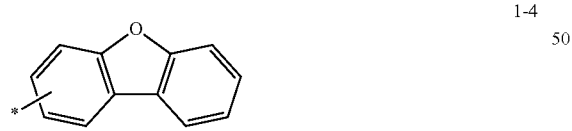

1-4

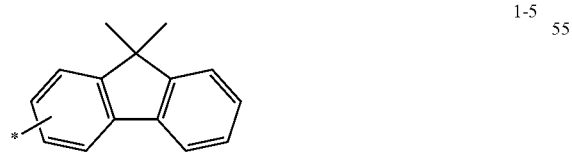

1-5

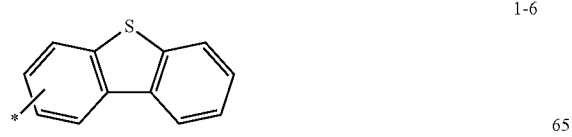

1-6

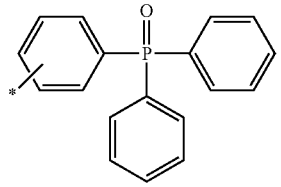

1-7

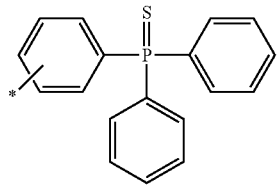

1-8

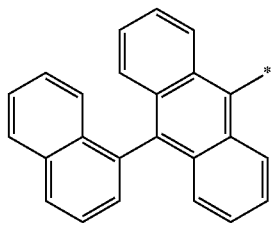

1-9

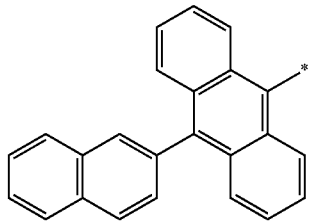

1-10

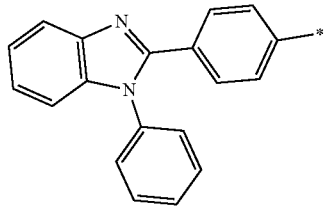

1-11

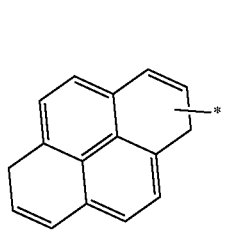

1-12

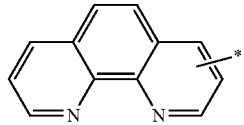

1-13

1-14
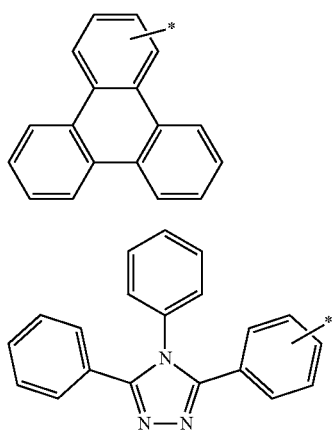
1-15
1-16
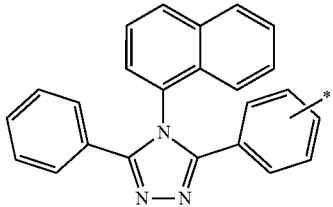
wherein, * denotes the binding sites of $R_{1-1}$, $R_{1-2}$, $R_{2-1}$, $R_{2-2}$, $R_{3-1}$ and $R_{3-2}$ with a benzene ring on the compound represented by the general formula I.
13. The display device according to claim 12, wherein the compound represented by the general formula I is selected from one of compounds 1 to 10:
Compound 1
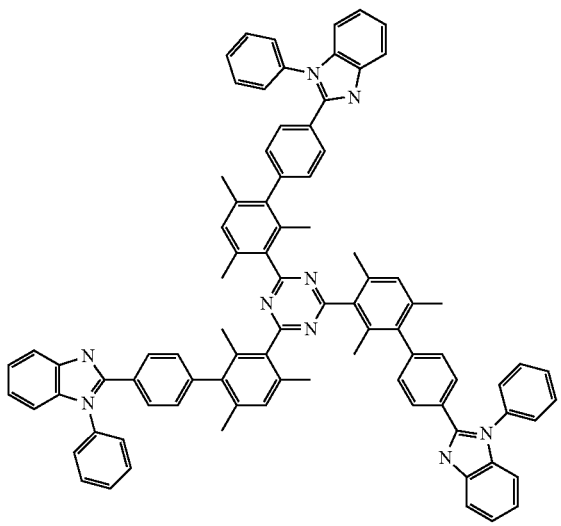
Compound 2
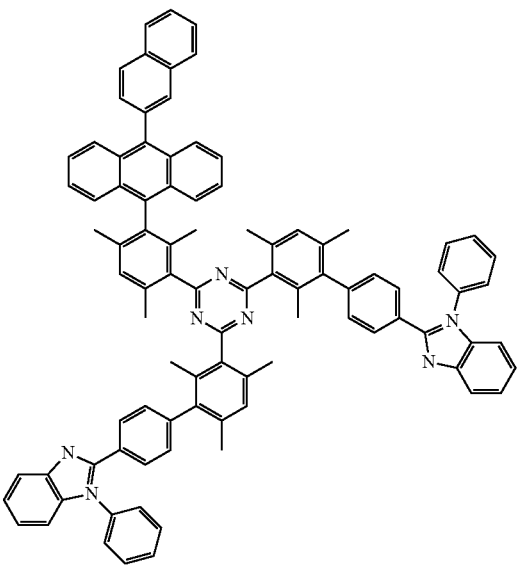
Compound 3
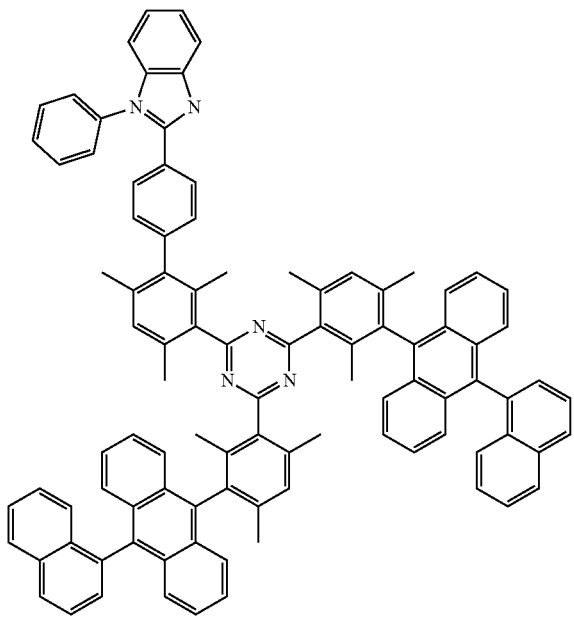

-continued
Compound 4
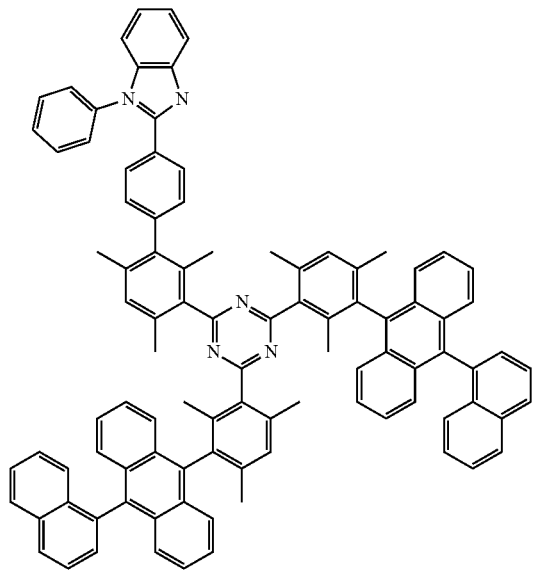
Compound 5
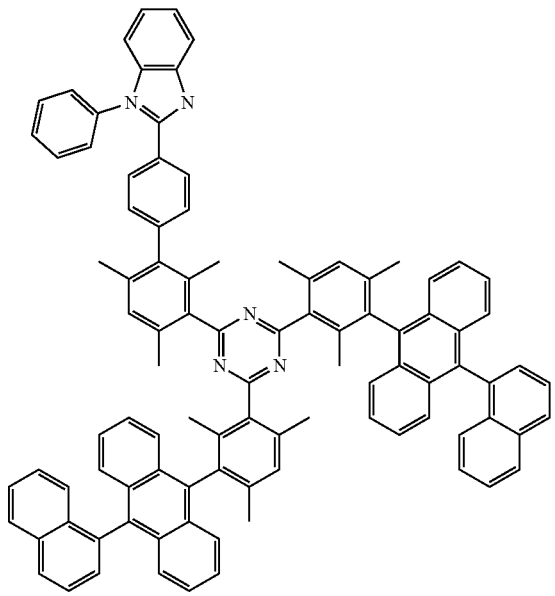
Compound 6
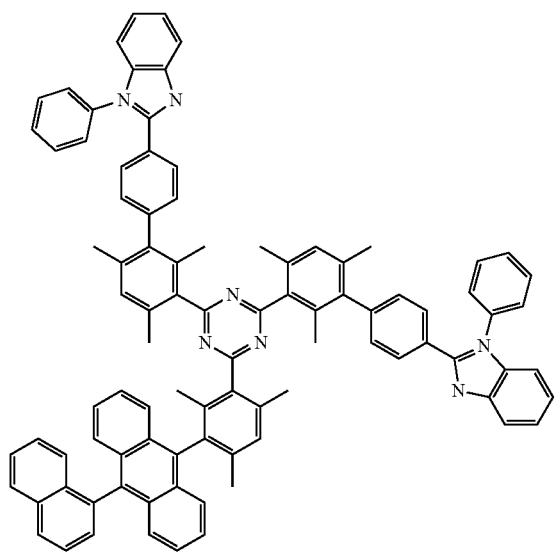
Compound 7
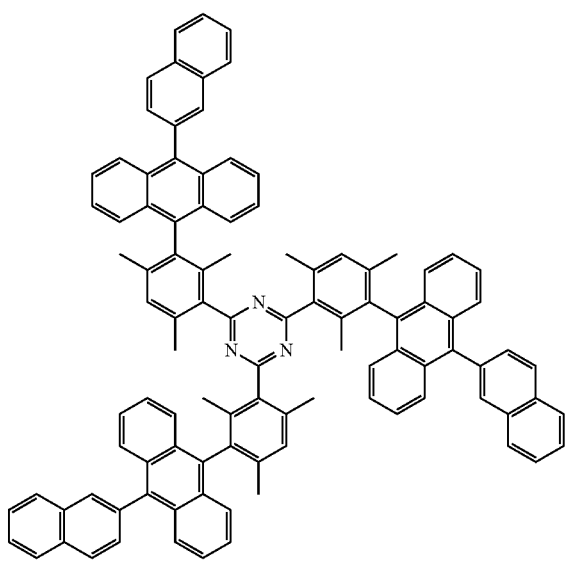

-continued

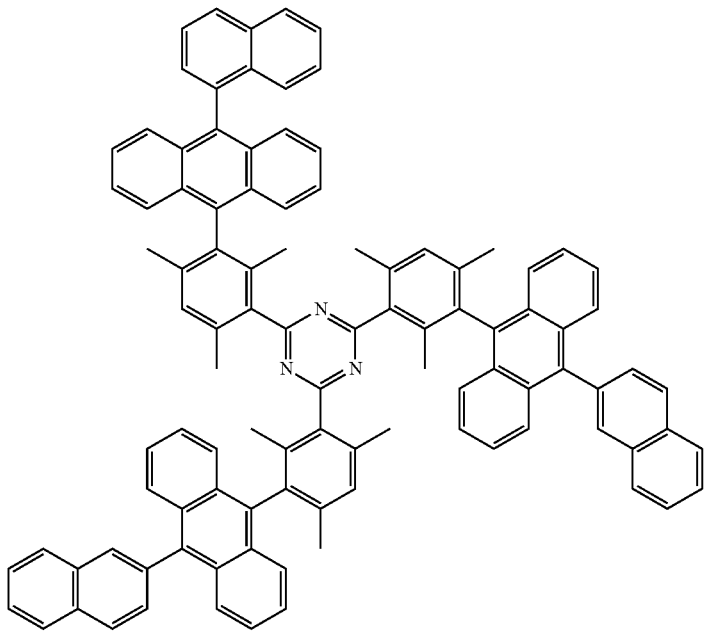
Compound 8

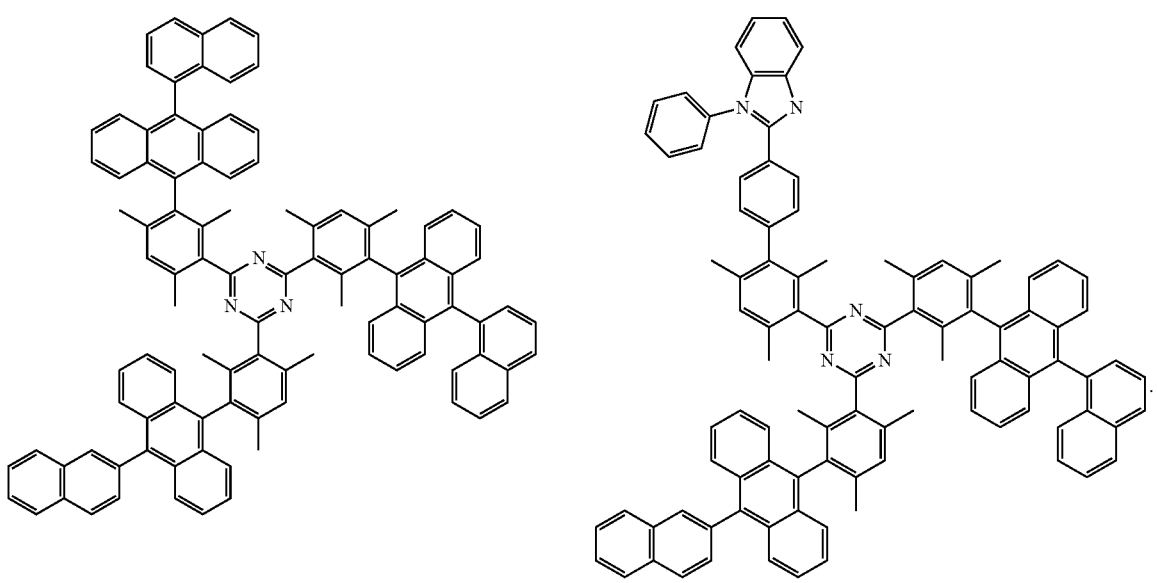
Compound 9

Compound 10

14. The display device according to claim 13, wherein the compound represented by the general formula I is selected from compound 1, compound 4 or compound 7.

15. The display device according to claim 12, wherein the display device is a bottom emitting type display panel.

16. The electron transport material according to claim 1, wherein $R_{1-1}$, $R_{1-2}$, $R_{2-1}$, $R_{2-2}$, $R_{3-1}$ and $R_{3-2}$ are each independently selected from hydrogen and one of the groups represented by formulas 1-3 and 1-7 to 1-16.

17. The electron transport material according to claim 1, wherein $R_{1-1}$, $R_{1-2}$, $R_{2-1}$, $R_{2-2}$, $R_{3-1}$ and $R_{3-2}$ are each independently selected from hydrogen and one of the groups represented by formulas 1-9 to 1-12 and 1-15 to 1-16.

* * * * *